US009078967B2

(12) United States Patent
Oerter et al.

(10) Patent No.: US 9,078,967 B2
(45) Date of Patent: Jul. 14, 2015

(54) BLOOD TREATMENT DEVICE

(75) Inventors: Goekhan Oerter, Weilmuenster (DE); Stefan Oesterreich, Neu-Anspach (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 0 days.

(21) Appl. No.: 13/635,209

(22) PCT Filed: Mar. 14, 2011

(86) PCT No.: PCT/EP2011/001260
§ 371 (c)(1),
(2), (4) Date: Sep. 14, 2012

(87) PCT Pub. No.: WO2011/113571
PCT Pub. Date: Sep. 22, 2011

(65) Prior Publication Data
US 2013/0015302 A1    Jan. 17, 2013

(30) Foreign Application Priority Data
Mar. 15, 2010  (DE) .......... 10 2010 011 464

(51) Int. Cl.
B62B 1/00      (2006.01)
A61M 1/16      (2006.01)
B62B 3/02      (2006.01)
B62B 5/04      (2006.01)

(52) U.S. Cl.
CPC .......... *A61M 1/1656* (2013.01); *B62B 3/02* (2013.01); *A61M 2209/084* (2013.01); *B62B 5/049* (2013.01); *B62B 2207/02* (2013.01)

(58) Field of Classification Search
CPC ........................... B62B 2206/02; B62B 3/144
USPC .......... 248/128, 129; 604/322; 280/656, 79.3, 280/46; 414/401, 389, 343, 344
See application file for complete search history.

(56) References Cited

U.S. PATENT DOCUMENTS

| 3,058,320 | A | * | 10/1962 | Foster et al. | 62/382 |
| 3,206,053 | A | * | 9/1965 | Bridge | 414/499 |
| 3,513,924 | A | * | 5/1970 | Jackson | 180/14.1 |
| 3,834,865 | A | * | 9/1974 | Lee | 432/241 |
| 4,096,920 | A | * | 6/1978 | Heyn | 180/11 |
| 4,487,461 | A | * | 12/1984 | Tindall et al. | 312/323 |
| 4,608,621 | A | * | 8/1986 | Porter | 361/827 |
| 5,072,960 | A | * | 12/1991 | Sperko | 280/47.34 |

(Continued)

FOREIGN PATENT DOCUMENTS

AU    4017885    9/1985
DE    19 39 932  6/1966

(Continued)

*Primary Examiner* — Terrell McKinnon
*Assistant Examiner* — Daniel Breslin
(74) *Attorney, Agent, or Firm* — Jacobson Holman, PLLC.

(57) ABSTRACT

A blood treatment device, in particular a dialyzer, configured to carry out a blood treatment, in particular a dialysis treatment, or a device configured for the filling of a mobile apparatus with and/or for the emptying of a mobile apparatus of a treatment fluid, in particular a dialysis fluid is provided. The device has at least one mount which is made such that a mobile apparatus can be received in the mount. The device has a guide element and/or a fixing element which are designed such that the mobile apparatus can be introduced into the mount and/or fixed in the mount with the aid of the guide element and/or of the fixing element.

19 Claims, 5 Drawing Sheets

(56) References Cited

U.S. PATENT DOCUMENTS

| | | | | |
|---|---|---|---|---|
| 5,193,831 | A * | 3/1993 | Capitoli | 280/202 |
| 5,320,475 | A * | 6/1994 | Pinder | 414/343 |
| 5,584,396 | A * | 12/1996 | Schmitt | 211/26 |
| 5,779,115 | A * | 7/1998 | Parkas et al. | 224/272 |
| 5,800,117 | A * | 9/1998 | Milton | 414/540 |
| 5,816,367 | A * | 10/1998 | Lilja et al. | 187/244 |
| 5,860,786 | A * | 1/1999 | Aubrecht | 414/463 |
| RE36,170 | E * | 3/1999 | Lilja et al. | 414/343 |
| 5,914,047 | A * | 6/1999 | Griffiths | 210/739 |
| 6,162,004 | A * | 12/2000 | Hanakawa | 414/389 |
| 6,283,698 | B1 * | 9/2001 | Lee | 414/537 |
| 6,364,326 | B1 * | 4/2002 | Reiland et al. | 280/33.993 |
| 6,418,011 | B2 * | 7/2002 | Omori | 361/679.33 |
| 6,585,828 | B1 * | 7/2003 | Kurita et al. | 134/8 |
| 6,651,993 | B1 * | 11/2003 | Emerzian et al. | 280/47.34 |
| 6,910,665 | B2 * | 6/2005 | Avendano et al. | 248/188.2 |
| 7,032,910 | B2 * | 4/2006 | Joie et al. | 280/47.131 |
| 7,128,330 | B2 * | 10/2006 | Krauss | 280/456.1 |
| 7,591,509 | B2 * | 9/2009 | Almy | 297/256.17 |
| 7,644,937 | B2 * | 1/2010 | Giampavolo et al. | 280/33.991 |
| 7,722,058 | B2 * | 5/2010 | Giampavolo | 280/33.991 |
| 7,871,088 | B2 * | 1/2011 | Silva et al. | 280/33.998 |
| 7,874,562 | B2 * | 1/2011 | Fitzgerald et al. | 280/47.34 |
| 8,006,786 | B1 * | 8/2011 | Chapman | 180/65.1 |
| 8,518,002 | B2 * | 8/2013 | Murray et al. | 604/319 |
| 2003/0090083 | A1 * | 5/2003 | Williams | 280/460.1 |
| 2004/0064080 | A1 | 4/2004 | Cruz et al. | |
| 2008/0230450 | A1 | 9/2008 | Burbank et al. | |
| 2008/0272564 | A1 * | 11/2008 | Fitzgerald et al. | 280/47.34 |
| 2010/0078092 | A1 | 4/2010 | Weilhoefer et al. | |

FOREIGN PATENT DOCUMENTS

| | | |
|---|---|---|
| DE | 103-13-965 | 10/2004 |
| DE | 10 2007 009269 | 8/2008 |
| WO | WO 99/00154 | 1/1999 |
| WO | WO 2008/104367 | 9/2008 |
| WO | WO 2008104367 A2 * | 9/2008 |

* cited by examiner

BLOOD TREATMENT DEVICE

This is a national stage of PCT/EP11/001260 filed Mar. 14, 2011 and published in German, which has a priority of German no. 10 2010 011 464.2 filed Mar. 3, 2010, hereby incorporated by reference.

BACKGROUND OF THE INVENTION

1. Field of the Invention

The present invention relates to a blood treatment device, in particular to a dialyzer, comprising means for the carrying out of a blood treatment, in particular a dialysis treatment, and/or to a device comprising means for the filling of a mobile apparatus with and/or for the emptying of a mobile apparatus of a treatment fluid, in particular a dialysis fluid.

2. Description of the Related Art

Dialyzers are known from the prior art in which the dialysis fluid is not prepared during a treatment, but in which rather the total amount of dialysis fluid required for a dialysis treatment is provided in a tank prior to the treatment. Dialyzers of this type are also called "batch-type" dialyzers.

It is furthermore known from the prior art in accordance with WO 2008/104367 A2 to connect these devices to a mobile unit in which the dialysis fluid is prepared and from which the prepared dialysis fluid is filled into the tank of the dialyzer.

Mobile apparatus for the transport of dialysis fluids are furthermore known from DE 103 13 965 B3 and from AU 40178/85.

It is the underlying object of the present invention to further develop a device of the initially named kind such that it can be connected in a simple and reliable manner to a mobile apparatus in which the treatment fluid, in particular the dialysis fluid, is present or which is to be filled with a treatment fluid.

SUMMARY OF THE INVENTION

This object is satisfied by a blood treatment device, in particular a dialyzer, having means for the carrying out of a blood treatment, in particular a dialysis treatment, or a device having means for the filling of a mobile apparatus with and/or for the emptying of a mobile apparatus of a treatment fluid, in particular a dialysis fluid. The device has at least one mount which is made such that a mobile apparatus can be received in the mount, with the device having guide means and/or fixing means which are made such that the mobile apparatus can be introduced into the mount and/or fixed in the mount with the aid of the guide means and/or of the fixing means. The term "device" includes any desired blood treatment device as well as any desired device by means of which the named mobile apparatus can be filled and/or emptied.

Provision is preferably made that the mobile apparatus is made with at least one tank in which a treatment fluid for the carrying out of the treatment is present or can be received.

The present invention furthermore relates to a mobile apparatus having at least one tank in which a treatment fluid, in particular a dialysis fluid, is present or can be received for the supply of a blood treatment device, in particular of a dialyzer, with the treatment fluid during a blood treatment carried out by the blood treatment device or for the connection to a device having means for the filling of the mobile apparatus with or for the emptying of the mobile apparatus of a treatment fluid, in particular dialysis fluid, wherein the mobile apparatus has guide means and/or fixing means which are made such that the mobile apparatus can be introduced into a mount of the device and/or can be fixed in a mount of the device with the aid of the guide means and/or the fixing means.

In the event that the mobile apparatus carries the total volume of dialysis fluid required for the treatment, the inherent weight of the mobile apparatus, including the weight of the dialysis fluid, can easily amount to up to 100 kg. It is conceivable that the mobile apparatus can be maneuvered by means of casters, with this having the advantage that the handling of the mobile apparatus is correspondingly simple in this manner despite its high weight and can be implemented practically in the daily routine of the clinic.

It is furthermore important that the mobile apparatus can be set up in a stationary and safe manner for reasons of safety and due to the risk of injury and that the mobile apparatus stands largely free of movement in the filling unit or emptying unit and in the treatment station.

Provision is preferably made that in those positions in which the mobile apparatus is connected to the device or forms its integral element after the moving into the mount, fluid-conducting line connections are present between the mobile apparatus and the device which may not be interrupted by mechanical influences such as vibrations, judders, etc. of the mobile apparatus or by its tank. It is equally conceivable that there are electronic/electrical connections between the mobile apparatus and the device which may not be interrupted by unwanted movements of the mobile apparatus.

It is generally conceivable that the device itself forms part of the stability since it can act as a support apparatus when the mobile apparatus is pushed in. It is possible in this manner largely to prevent a lateral unsteadiness by these support apparatus.

Provision is furthermore preferably made that precautions are taken against the rolling away of the mobile apparatus from its position introduced into the mount. It is conceivable to use lockable casters which can be locked after the introduction of the mobile apparatus into the mount of the device.

If the locking is inadvertently not actuated, there is, however, the risk that the mobile apparatus is moved out of its intended position or rolls away from it in an unwanted manner.

To ensure a simple introduction of the mobile apparatus into the mount and/or to hold the mobile apparatus in the desired position, guide means and/or fixing means are provided at the device and/or at the mobile apparatus.

The guide means can, for example, be made as a guide tongue or as a rail or as any other guide. This guide tongue or guide means provides a good possibility to introduce the comparatively heavy, filled mobile apparatus into the blood treatment device or the filling unit or emptying unit without the mobile apparatus and the device being able to get caught up with one another and thus perhaps being able to damage the construction.

The guide means and in particular the named guide tongue preferably have a groove or other guide track in which or on which a counter-piece of the respective other part, that is, of the device or of the mobile apparatus, runs.

The groove or guide track is preferably located on the upper side of the guide tongue.

Provision is made in a further embodiment of the invention that the guide means and/or the fixing means, in particular the groove or guide track, have at least one recess. This recess can form an element of the fixing means such that an element of the respective other apparatus, that is, either of the device or of the mobile apparatus, engages into the recess when the mobile apparatus is in its desired, introduced position in the mount.

The recess is preferably arranged at the groove end or at the end of the guide track.

Provision is made in another embodiment of the invention that the groove has at least one introduction opening which has a larger width than the part of the groove or track adjoining the introduction opening in the direction of introduction. It is possible in this manner to compensate irregularities during the docking of the mobile apparatus by the user.

Provision is made in a further embodiment of the invention that there is a direction of introduction in which the mobile apparatus can be introduced into the mount of the device, with provision being able to be made that the guide tongue extends in the direction of introduction. It is, for example, conceivable that the blood treatment device or the filling unit or emptying unit has an open side into which the mobile apparatus can be introduced in a direction of introduction and that the named guide tongue extends in the direction of introduction.

Provision is made in a further embodiment of the invention that the fixing means include means for the shape-matched fixing, in particular comprise latch means or consist thereof.

Provision can furthermore be made that the fixing means and/or guide means comprise at least one ball transfer unit or ball or roll or a slide piece or a blade piece.

It is conceivable to arrange this roll, ball or caster, blade or slide piece at the lower side of the mobile apparatus and to allow it to engage into the recess of the guide tongue when the mobile apparatus has reached its desired end position.

Provision is preferably made that only a comparatively small force effort is required when the fixing means are coupled or uncoupled. This can be realized by the named ball transfer unit or by a ball, roll, slide piece or blade piece or the like which is preferably dimensioned such that it can be introduced into the recess when the mobile apparatus has reached its desired end position.

It is conceivable to arrange this roll, ball or caster, blade or slide piece at the lower side of the mobile apparatus and to allow it to engage into the recess off the guide tongue when the mobile apparatus has reached its desired end position.

Provision is made in a further embodiment of the invention that the device and/or the mobile apparatus has one or more support feet and/or one or more casters.

Provision is furthermore made in a preferred embodiment of the invention that the casters, preferably the casters located at the front in the insertion direction, or also all the casters of the mobile apparatus, are designed as flat and as not pivoting outwardly where possible or pivoting outwardly only a little so that a catching of the casters with the blood treatment device is avoided where possible. The casters or wheels of the mobile apparatus are preferably designed in accordance with DE 19 39 923 A1, to which reference is made in this respect. Accordingly, the casters or wheels comprise a rotatably arranged hub body which has a plurality of rotatable casters which project on its periphery beyond the hub body periphery and whose axes of rotation extend in the direction of the tangents at the hub body periphery. It is possible by this design also to move the mobile apparatus easily in directions perpendicular to one another in the loaded state.

Reference is made with respect to further conceivable embodiments of the casters or wheels to DE 19 39 923 A1, which is in this respect included in the disclosure content of the present invention.

This movability (bidirectional or multidirectional) of the caster can apply only to the casters trailing on the introduction into the mount, only to the casters at the front on the introduction into the mount or both to the trailing and to the front casters of the mobile apparatus.

It is conceivable that the device has one or more support feet at the open side of the side facing the mount or one or more casters at the open side of the side remote from the mount.

The present invention furthermore relates to a system having at least one device and having at least one mobile apparatus in accordance with one of the preceding claims.

Provision is preferably made that the guide means are made such that the mobile apparatus is raised into the mount of the device at its side directed to the device at least at the start of the introduction movement.

This has the result that the mobile unit is easier to maneuver, which brings along the advantage that it can be moved into the mount in a defined and unerring manner.

Provision can furthermore be made that the device is raised at its side directed to the open side of the mount when the mobile apparatus has been introduced into the mount.

The present invention furthermore relates to a method for the introduction of a mobile apparatus into a device, wherein the mobile apparatus is raised at its side facing the device on the introduction into the device so that the weight of the mobile apparatus is also carried by the device. The likelihood of a displacement of the device preferably at the start of the introduction process by pressing the support feet or casters to the floor is thereby reduced, that is, a braking effect is exerted when the mobile apparatus acts, for example, on the guide means and/or on the fixing means.

The invention furthermore relates to a method for the introduction of a mobile apparatus into a device, wherein the device carries out a tilt movement on the introduction of the mobile apparatus into the mount of the device and is raised at its side facing the introduction side of the mount after the introduction of the mobile apparatus into the mount of the device.

The device is preferably slightly inclined toward its introduction side before the introduction of the mobile apparatus.

If the mobile apparatus is now pushed in, it or its slide caster or the like presses increasingly more powerfully onto the device or onto its guide means and/or fixing means as the pushing in progresses so that the device tilts out of its inclined position into a preferably straight position. In this process, the front feet, that is, the feet inclined toward the introduction side, in particular the carrying feet of the device, are raised. The device thus only stands on the two rear feet or preferably on the two rear casters.

Since the device, however, forms a unit with the mobile apparatus after the introduction thereof, the device is stable.

If the weight of the device and of the mobile apparatus in the inserted state is only carried by casters, this total unit of device and mobile apparatus is thus displaceable.

BRIEF DESCRIPTION OF THE DRAWINGS

Further details and advantages of the invention will be explained in more detail with reference to an embodiment shown in the drawing. There are shown.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
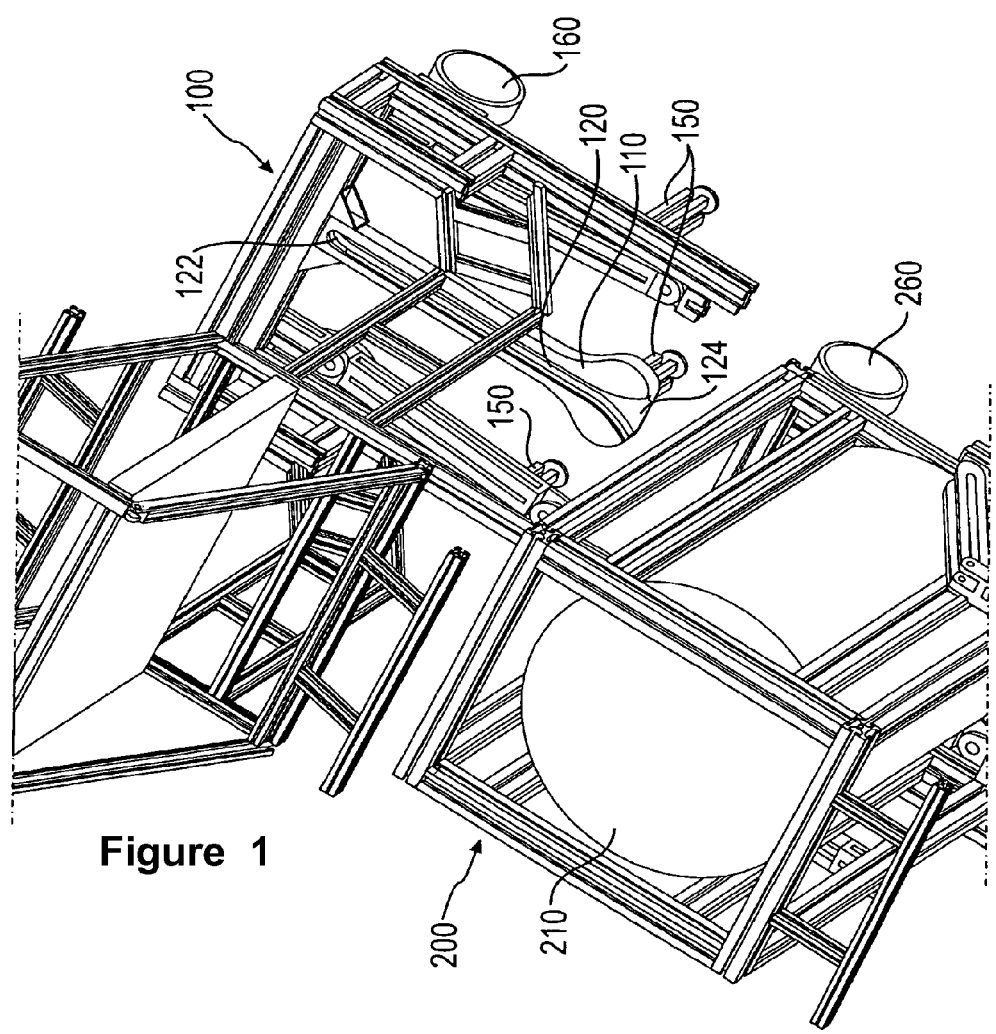
FIG. 1: a perspective view of a blood treatment device and of a mobile apparatus with tank before the introduction of the mobile apparatus.

In FIG. 1, a blood treatment device is marked by the reference numeral 100 and is a dialyzer 100 which has means, not shown in any more detail in the drawing, for the carrying out of a blood treatment, in particular of a dialysis treatment. These means can, for example, have an extracorporeal blood circuit or the hoses and pumps, at least one dialysis machine, etc. required for this purpose.

As can be seen from FIG. 1, the blood treatment device 100 has a U-shaped frame which is open at one side, with the open side of the frame representing the introduction side for the introduction of the mobile apparatus 200. The mount of the device 100 has a width so that the mobile apparatus 200 can be pushed into the mount. The mobile apparatus 200 has a tank 210 in which treatment fluid for the carrying out of the treatment, in particular a dialysis fluid, is received.

Trestle rollers arranged in the rear region of the blood treatment device 100 are marked by the reference numeral 160. Support feet which extend in the region of the blood treatment device 100 which is directed toward the introduction side are marked by the reference numeral 150. As can be seen from FIG. 1, one of the support feet 150 extends on the lower side of a guide tongue 110 which extends in the direction of introduction and thus perpendicular to the plane of introduction or perpendicular to the open side of the blood treatment device 100. Trestle rollers of the mobile apparatus 200 are represented by the reference numeral 260. They can be made steerable or rolling bidirectionally or multidirectionally or also rigid and only rolling in one direction. Reference is made accordingly to the above statements on DE 19 39 932 A1.

Figure 4:
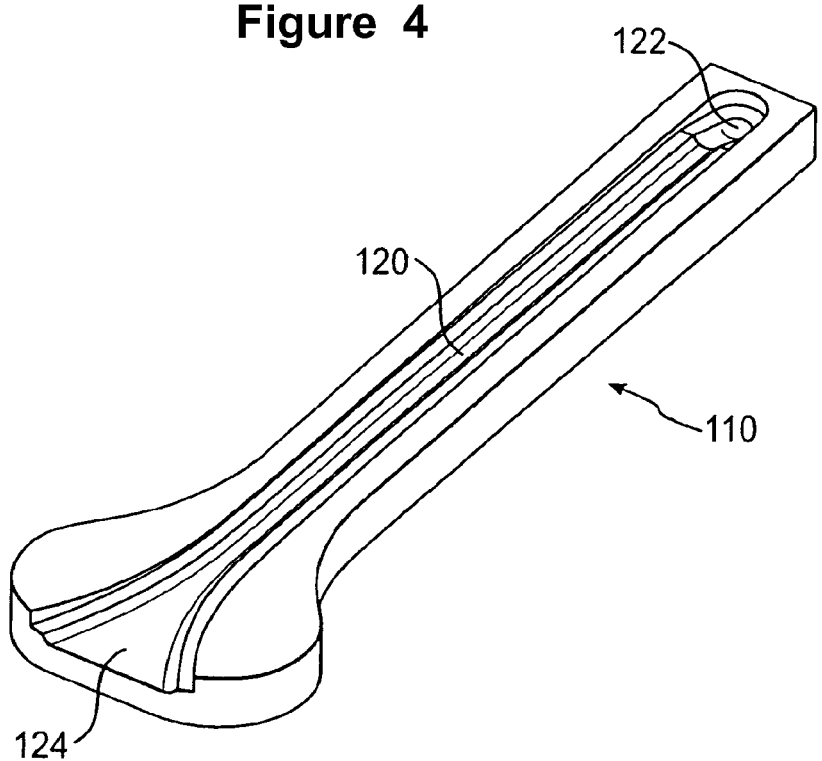
FIG. 4: a perspective representation of the guide tongue of the blood treatment device.

As can in particular be seen from FIG. 4, the guide tongue 110 has a groove 120 which extends in the direction of introduction and which has a comparatively wide introduction opening 124.

The guide tongue 110 is made in a freely projecting manner and preferably has a rounded portion at its free end.

A recess 122 which is set back downwardly with respect to the groove base and which serves for the reception of a ball or ball transfer unit of the mobile apparatus 200 not visible from FIG. 1 is located in the region of the rear groove end.

Figure 2:
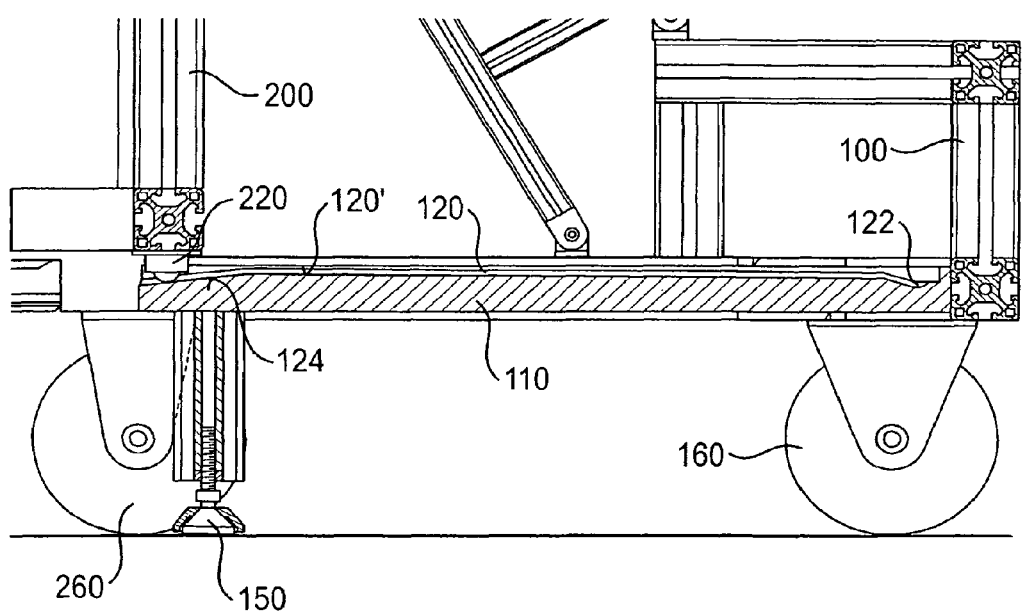
FIG. 2: a schematic side view of the lower region of the blood treatment device before introduction of the mobile apparatus.

FIG. 2 shows a side representation in a schematic view. It can be recognized from this representation that the groove 120 has a groove base 120' which rises slightly in the region of the introduction side shown at the left and which merges into the named recess 122 in its rear end shown at the right.

Figure 3:
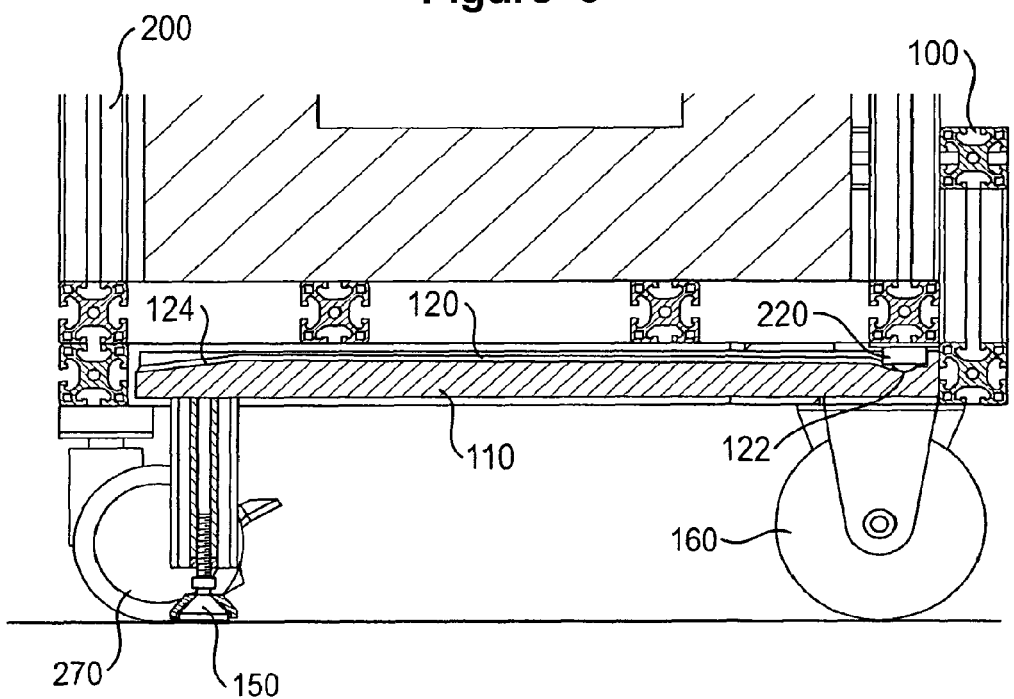
FIG. 3: a schematic side view of the lower region of the blood treatment device with a mobile apparatus introduced.

A ball transfer unit is marked by the reference numeral 220 which is arranged at the mobile apparatus 200 such that it can be introduced into the groove 120 and is arranged in the recess 122 in the completely introduced state as can be seen from FIG. 3. It can furthermore be seen from FIG. 3 that the mobile apparatus 200 likewise has casters 270 at its end trailing in the direction of introduction. They are preferably made pivotable and/or rolling bidirectionally or multidirectionally, as was described above in more detail, in particular with reference to DE 19 39 923 A1.

The guide tongue 110 can, for example, be designed as a milled part, but also be made differently. In the embodiment shown here, it is the central guide element located at the middle of the mount and it ensures a defined docking movement of the mobile apparatus 200 into the mount of the blood treatment device 100 or into the mount of a filling device or of an emptying device which are not shown in the drawings.

The guide tongue 110 is fixedly installed at one of the device components, in the embodiment at the blood treatment device 100.

As can be seen from FIG. 4, the guide tongue 110 has a guide geometry which enables an interaction with the ball transfer unit 220.

The ball transfer unit 220 is a fixed element of the further device components, in the present embodiment it is a fixed element of the mobile apparatus 200.

As stated above and as can be seen in FIG. 1, the guide tongue 110 has a comparable wide opening 124 of the groove. This wide opening 124 ensures that the ball transfer unit 220 can be moved securely on the track or in the groove 120 of the guide tongue 110.

FIG. 2 shows the start of docking. The ball transfer unit 220 first impinges on the opening 124 of the groove 120 of the guide tongue 110. The blood treatment device 100 or the filling unit or emptying unit is in this condition, that is, in a state slightly inclined to the front, i.e. toward the mobile apparatus 200, at the start of the docking movement.

This has the result that the height level of the guide tongue 110 in the region of its opening 124 is below the level of the ball transfer unit 220. As the push-in movement progresses, the level of the groove 120 or of the guide track rises, which has the result that the trestle rollers 260 at the rear side of the mobile apparatus 200 in FIG. 2 are raised from the floor.

This has the result that the mobile apparatus 200 is only still movable with the ball transfer unit 220 and the front axis not shown in FIG. 2 and preferably allowing a pivot movement or bidirectional or multidirectional movement or the other support elements and thereby has enough movement freedoms to be moved into the device 100 in a defined and unerring manner.

A further substantial advantage of the raising of the mobile apparatus 200 at the side directed toward the device 100 comprises the fact that the weight of the mobile apparatus 200 is partly taken over by the device 100, which has the result that a braking effect is exerted via the support foot 150 which extends at the guide tongue 110.

FIG. 3 shows the end of the docking movement at which the mobile apparatus 200 is located completely in the mount.

As can be seen from FIG. 3, the ball transfer unit 220 moves over a ramp down into a recess 122 and is received in the recess 122 at the end of the docking movement. In this respect, the support feet 150 of the device 100 are raised from the ground since the device 100 is tilted slightly to the rear. This has the result that the roller 260 of the mobile apparatus 200 is now seated on the ground again since the levels of both components (device and mobile apparatus) are matched at the end by the ramp of the guide groove 120.

Figure 5:
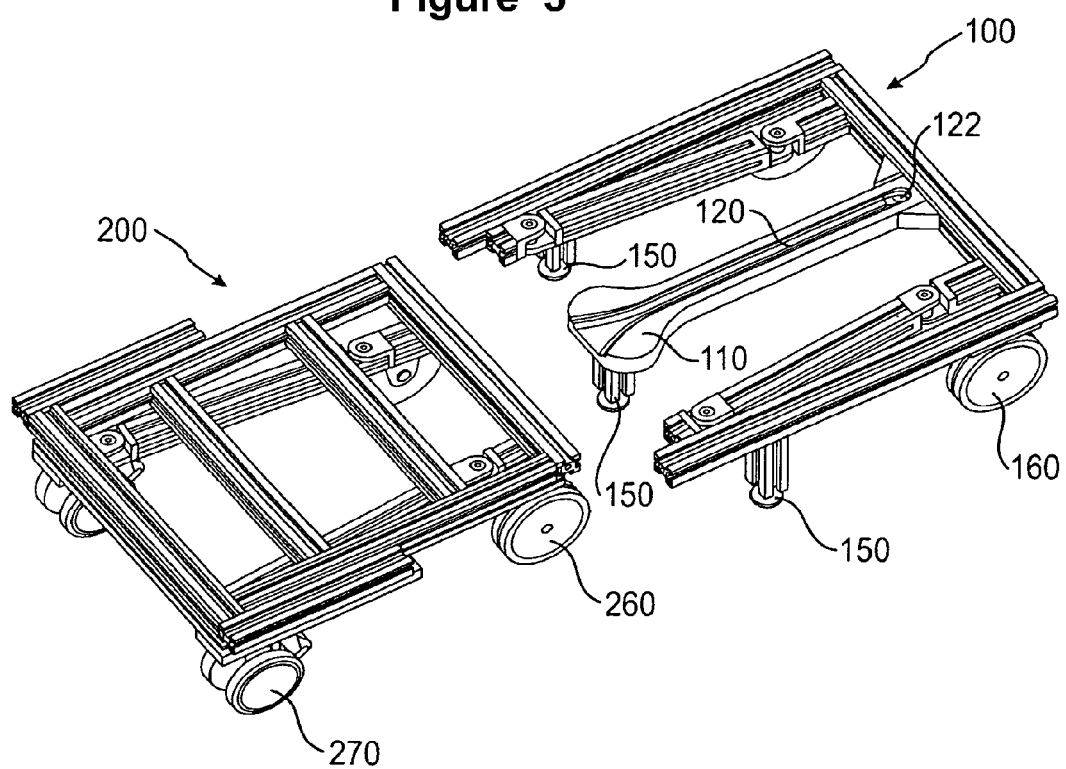
FIG. 5: a perspective view of a blood treatment device and of a mobile apparatus without a tank before the introduction of the mobile apparatus.

FIG. 5 shows an embodiment of the present invention comparable with the arrangement in accordance with FIG. 1. The arrangements in accordance with FIG. 1 and FIG. 5 differ in that the mobile apparatus 200 in accordance with FIG. 5 does not have a tank.

As can further be seen from FIG. 5, the mobile apparatus 200 has rollers 260, 260' not only at its leading side directed toward the dialyzer 100, but also toward its trailing side.

Furthermore, parts in accordance with FIG. 5 which are the same or which have the same function are marked by the same reference numerals as in FIG. 1. As can further be seen from FIG. 5, the mobile apparatus 200 in accordance with this embodiment only stands on rollers 260, 270, whereas the dialyzer 100, which is only shown in its basic structure in FIG. 5, only has rollers 160 on the side remote from the introduction opening, that is, the rear region, and otherwise has support feet 150. A corresponding embodiment and arrangement of rollers and support feet is also conceivable for the further embodiments of the invention and is not restricted to the arrangement in FIG. 5.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A mounting structure for a blood treatment device that is configured to carry out a blood treatment, or for a device configured to fill a mobile apparatus with and/or to empty a mobile apparatus of a treatment fluid for the blood treatment, the device mounting structure comprising:
    said device having at least one mount with an open side configured to receive a mobile apparatus, said device having a first support element at said open side and a second support element on a side remote from the open side, said device tilted downwardly toward the open side when all of said support elements are on the ground;
    a guide element and/or fixing element including a groove or guide track to introduce the mobile apparatus into the mount through said open side of the mount and/or to fix the mobile apparatus in the mount, said mobile apparatus pressing down on said groove or guide track as the mobile apparatus is introduced into the open side of the device so that, as introduction begins, part of the weight of said mobile apparatus is supported by at least said device first support element, said groove or guide track rising in a direction of introduction, the mobile apparatus, when pushed further into the device to complete the introduction, causing the side of the device directed toward the open side of the mount to be tilted upwardly to raise the first support element off the ground when the mobile apparatus is fully introduced into said mount.

2. The device mounting structure in accordance with claim 1, wherein the guide element and/or the fixing element include at least one guide tongue and/or at least one guide rail.

3. The device mounting structure in accordance with claim 2, wherein the groove or guide track is arranged in the guide tongue.

4. The device mounting structure in accordance with claim 3, wherein the groove or guide track has at least one recess.

5. The device mounting structure in accordance with claim 4, wherein the recess is arranged at an end of the groove or at an end of the guide track.

6. The device mounting structure in accordance with claim 2, wherein an introduction opening is present in which the mobile apparatus can be introduced into the mount of the device, said guide tongue extending in the introduction opening.

7. The device mounting structure in accordance with claim 1, wherein the groove or the guide track has at least one introduction opening which has a larger width than a remaining part of the groove or of the guide track.

8. The device mounting structure in accordance with claim 1, wherein the first and second support elements of the device include one or more support feet and/or one or more rollers.

9. The device mounting structure in accordance with claim 8, wherein the first support element includes one or more support feet and the second support element includes one or more rollers.

10. A mobile apparatus having at least one tank in which a treatment fluid is present or can be received for the supply of a blood treatment device with the treatment fluid during a blood treatment carried out by the blood treatment device or for the connection to a device configured to fill the mobile apparatus with or to empty the mobile apparatus of a treatment fluid, said mobile apparatus comprising front support elements, trailing support elements and a guide element and/or a fixing element including at least one ball, roller, blade or slide piece that engages with a groove or guide track in the device to introduce the mobile apparatus into a mount of the device and/or to fix the mobile apparatus in said mount with the aid of the guide element and/or the fixing element, said mount having an open side into which the mobile apparatus is introduced starting with the front support element side, a side of the device directed toward the open side of the mount having support elements that are on the ground when introduction of the mobile apparatus begins, said mobile apparatus and said guide element and/or said fixing element being configured to raise said side of the device directed toward the open side of the mount to bring the device support elements off the ground when the mobile apparatus is fully introduced into said mount while said trailing support elements of said mobile apparatus stay on the around.

11. The mobile apparatus in accordance with claim 10, wherein the ball or the roll or the blade or the slide piece is dimensioned such that it can be introduced at least partly into a recess of the guide element.

12. A system configured to support a blood treatment, said system comprising:
    a device that is configured to carry out a blood treatment or to fill a mobile apparatus with and/or to empty a mobile apparatus of a treatment fluid for the blood treatment, said device having a first support element at an introduction side and a second support element on a side of said device remote from the device introduction side;
    a mobile apparatus having at least one tank in which a treatment fluid is present or can be received for the supply of the device with the treatment fluid during a blood treatment carried out by the device;
    said device having at least one mount with an open side on said introduction side configured to receive said mobile apparatus, said device tilting downwardly toward said open side when all of said device support elements are on the ground; and
    a guide element and/or fixing element including a first element on said device that cooperatively engages with a second element on said mobile apparatus to introduce the mobile apparatus into the mount through said open side of the device and/or to fix the mobile apparatus in the mount, said mobile apparatus second element engaging said device first element as the mobile apparatus is introduced into the open side of the mount so that, as introduction begins, the weight of said mobile apparatus is at least partly supported by said device first support element, said guide element and/or said fixing element guiding the mobile apparatus as the mobile apparatus is pushed further into the mount, a side of the device directed toward the open side of the mount being tilted upwardly by the mobile apparatus to raise the first support element off the ground when the mobile apparatus is fully introduced into said mount.

13. The system in accordance with claim 12, wherein the first element of said guide element and/or fixing element includes a groove or guide track that raises a side of the mobile apparatus directed toward the device when the mobile apparatus is being introduced into the mount of the device, said second element of said guide element and/or fixing element including a rolling or sliding component that moves along the groove or guide track as the mobile apparatus is introduced into the device.

14. The system in accordance with claim 13, wherein the sliding or rolling element is dimensioned such that it can be introduced at least partly into a recess in the groove or guide track.

15. The system as set forth in claim 12, wherein the first element of said guide element and/or the fixing element includes at least one guide tongue and/or at least one guide rail and the second element includes at least one ball, roller, blade or slide piece.

16. The system as set forth in claim 15, wherein the first element of said guide element and/or the fixing element includes at least one groove or guide track arranged in the guide tongue, said second element sized to cooperatively engage with said groove or guide track.

17. The system as set forth in claim 16, wherein the groove or guide track has at least one recess arranged at an end of the groove or at an end of the guide track, said second element dropping into said at least one recess when introduction is complete to fix the mobile apparatus to the mount.

18. A method of mounting a mobile apparatus onto a blood treatment device that is configured to carry out a blood treatment, or onto a fluid device configured to fill a mobile apparatus with and/or to empty a mobile apparatus of a treatment fluid for the blood treatment, said device having a mount with an open side configured to receive said mobile apparatus, said device having a first support element on an introduction side that is directed toward said mount open side and a second support element on a device side remote from the introduction side, said device tilted downwardly toward the introduction side when said first and second support elements are on the ground, said device including a groove or guide track inclined upwardly in a direction of introduction, said mobile apparatus having at least one tank in which a treatment fluid is present or can be received for the supply of the blood treatment device with the treatment fluid during a blood treatment carried out by the blood treatment device, said mobile apparatus having front supports and trailing supports, and a guide element and/or fixing element including at least one rolling or sliding component that engages with the groove or guide track of the device to introduce the mobile apparatus into the open side of the mount and/or to fix the mobile apparatus in the mount, said method comprising the steps of:

starting introduction of said mobile apparatus into the open side of the mount, front supports first, said device tilted toward the introduction side with the first support element being on the ground when the mobile apparatus is starting to be introduced into the mount of the device, the guide element raising the front support side of the mobile apparatus directed toward and entering the device so that at least a part of a weight of the mobile apparatus is carried by the device, the first and second support elements of the device still being on the around;

continuing the introduction of the mobile apparatus by pushing the mobile apparatus closer to the side of the device remote from the introduction side; and as the front supports of the mobile apparatus come near to the side of the device remote from the introduction side, said device tilting as said rolling or sliding component moves upwardly in said groove or guide track, the introduction side of the device being raised when the mobile apparatus is fully introduced into said mount so that said device first support element is lifted up off the ground.

19. The system in accordance with claim 18, wherein said rolling or sliding component includes at least one ball, roller, blade or slide piece sized to cooperatively engage with said groove or guide track.

* * * * *